United States Patent [19]

Chiang

[11] Patent Number: 5,043,181
[45] Date of Patent: Aug. 27, 1991

[54] METHOD OF USING PYRIDINE ANALOGUES OF SACCHARIN FOR SWEETENING

[75] Inventor: George Chih-shu Chiang, Wilmington, Del.

[73] Assignee: E. I. du Pont de Nemours and Company, Wilmington, Del.

[21] Appl. No.: 425,401

[22] Filed: Oct. 23, 1989

[51] Int. Cl.⁵ .............................................. A23L 1/236
[52] U.S. Cl. ..................................... 426/548; 546/114
[58] Field of Search ....................... 546/114; 426/548; 548/108

[56] References Cited

U.S. PATENT DOCUMENTS

| | | |
|---|---|---|
| 319,082 | 6/1985 | Fahlberg . |
| 2,275,125 | 3/1942 | Audrieth et al. . |
| 3,294,551 | 12/1966 | Herbst . |
| 3,492,131 | 1/1970 | Schlatter . |
| 3,965,107 | 6/1974 | Rainey et al. ....................... 546/114 |
| 4,001,455 | 1/1977 | La Via et al. ....................... 426/548 |
| 4,404,230 | 9/1983 | Trummlitz et al. ................. 426/548 |
| 4,419,346 | 12/1983 | Stroz et al. .......................... 426/548 |
| 4,728,732 | 3/1988 | Skotnicki et al. ................... 540/227 |

FOREIGN PATENT DOCUMENTS 308371  3/1989  European Pat. Off. .

*Primary Examiner*—Donald E. Czaja
*Assistant Examiner*—A. J. Weier
*Attorney, Agent, or Firm*—William H. Hamby

[57] ABSTRACT

This invention concerns compounds that are pyridine analogues of saccharin and that are synthetic sweeteners, compositions containing them, and their methods of use as sweetening agents.

3 Claims, No Drawings

METHOD OF USING PYRIDINE ANALOGUES OF SACCHARIN FOR SWEETENING

FIELD OF THE INVENTION

This invention relates to synthetic sweeteners and their use of sweetening agents. More particularly, this invention relates to pyridine analogues of saccharin as sweeteners, various compositions containing them, and their use thereof.

BACKGROUND OF THE INVENTION

Synthetic sweeteners are known in the art and are described in U.S. Pat. No. 3,294,551 (cyclamates), U.S. Pat. No. 319,082 (saccharin), U.S. Pat. No. 2,275,125 (cyclamates) and U.S. Pat. No. 3,492,131 (aspartame). EP-A 308,371 discloses 4-$A_3$a-saccharrin.

However, previously developed synthetic sweeteners often exhibit a strong and disagreeable aftertaste or a relatively short storage life before losing all or part of their sweet character.

It is an object of the present invention to provide a synthetic sweetener that has a palatable aftertaste. It is a further object of the present invention to provide a synthetic sweetener with a long storage life, making it ideal for incorporation into packaged foods and beverages. A feature of the present invention is its ease of synthesis. An advantage of the present invention is that it can be readily processed into a variety of forms including tablets, powders, and syrups. These and other objects, features and advantages will become apparent upon having reference to the following description of the invention.

SUMMARY OF THE INVENTION

This invention comprises compounds of Formula I:

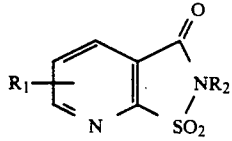

and suitable salts thereof,
wherein
$R_1$ is H, Cl, F, Br, $CH_3$, $OCH_3$, or $CF_3$; and
$R_2$ is H or $C_1$–$C_4$ alkyl.

Preferred for their superior sweetening ability and/or ease of synthesis are:
1. Compounds of Formula I wherein $R_2$ is H.
2. Compounds of Preferred 1 wherein $R_1$ is H.

The invention further discloses compositions suitable as sweetening agents comprising the aforementioned compounds. The invention still further contemplates a method for sweetening foods and beverages, comprising the addition thereto of the aforementioned compounds.

DETAILS OF THE INVENTION

Compounds of Formula I have been shown to be synthetic sweeteners. They are sweet to the taste and do not suffer from the bitter aftertaste of the known saccharin sweeteners. The rat oral approximate lethal dose (ALD) of 11,000 mg/kg for Compound I ($R_1 = R_2 = H$) demonstrates an excellent toxicological profile. In addition, the compounds of Formula I are thermally and chemically stable. The compounds of Formula I may be prepared as outlined in Scheme I.

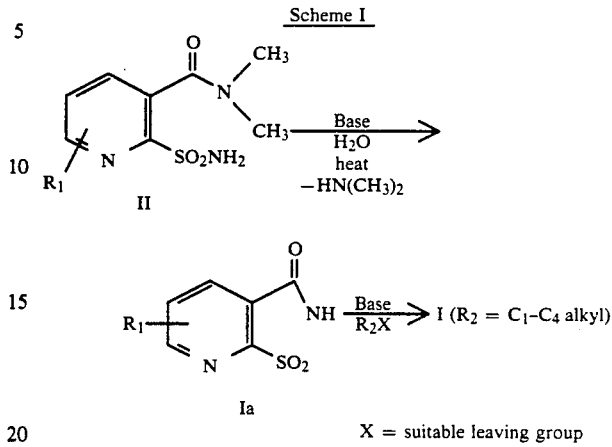

X = suitable leaving group

The starting pyridine sulfonamide II are known in the art and can be prepared according to procedures described in U.S. Pat. No. 4,786,734 or EP-A-237,292.

Typical, but not limiting reaction conditions are as follows in Table I.

TABLE I

| Variable | Range | Preferred |
| --- | --- | --- |
| Temperature | 0 to 150° C. | 75–100° C. |
| Solvents | water-miscible | water, alcohol/water, dimethylsulfoxide, dimethylformamide, tetrahydrofuran, ether or benzene or mixtures of all the above with water in a range of 0.01:1 to 1:0.01. |
| Molar ratio (II:Base) | 1:0.8 to 1:10 | 1:0.9 to 1:2.5 |
| Base | Metal earth hydroxides, alkoxides, alkyl lithiums and hydrides | NaOH, KOH, LiOH NaH, KH, BuOK, BuLi, t-BuLi, $NaOCH_3$, $KOCH_3$. |
| Pressure | 1 to 3 atm | 1 atm |

EXAMPLE 1

Preparation of Pyrido(a-b)isothiazol-4-one 2,2-dioxide (Compound I, $R_1 = R_2 = H$)

To a 500 mL round-bottomed flask equipped with a mechanical stirrer and a reflux condenser was charged 22.9 g (0.1 mole) of N,N-dimethyl-2-amino-sulfonyl-3-pyridinecarboxamide, 200 mL water and 8 g 50% NaOH. After stirring for a few minutes, a clear solution was formed. It was heated to reflux for 3 hours. During reflux, dimethylamine was evolving out of the reactor and was scrubbed. The condenser was removed and the reaction temperature was kept at 90° C. to allow more dimethylamine to evolve to the scrubber. After 2 hours at 90° C., the reaction mixture was cooled to 10° C. The pH of the reaction solution was adjusted with HCl to acidic (ca. 2) and solids began to crystallize out. Filtration afforded the desired product which weighed 9 g after drying at 70° C. overnight. The filtrate after standing overnight crystallized more product which was recovered by filtration.

NMR (δ, CDCl₃), 7.6 (s, 1H), 7.9 (dd, 1H), 8.4 (d, 1H), 9.0 (d, 1H).

IR: 1730 cm-1 and 1700 cm-1 indicating 5-membered isothiazolone ring.

Mass Spec. (m/z) showing M+1, 185,

Using the procedures described above or obvious variations thereof, the following compounds may be prepared.

TABLE II

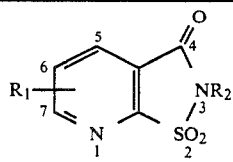

| R₁ | R₂ |
|---|---|
| H | H |
| H | CH₃ |
| H | CH₂CH₃ |
| H | CH₂CH₂CH₃ |
| H | CH(CH₃)₂ |
| H | CH(CH₂)₃CH₃ |
| 5-Cl | H |
| 5-F | H |
| 5-Br | H |
| 5-CH₃ | H |
| 5-OCH₃ | H |
| 5-CF₃ | H |
| 6-Cl | H |
| 6-F | H |
| 6-Br | H |
| 6-CH₃ | H |
| 6-OCH₃ | H |
| 6-CF₃ | H |
| 7-Cl | H |
| 7-F | H |
| 7-Br | H |
| 7-CH₃ | H |
| 7-OCH₃ | H |
| 7-CF₃ | H |
| 5-Cl | CH₃ |
| 5-Br | CH₃ |
| 5-CH₃ | CH₃ |
| 5-OCH₃ | CH₃ |
| 5-CF₃ | CH₃ |
| 6-Cl | CH₃ |
| 6-Br | CH₃ |
| 6-F | CH₃ |
| 6-CH₃ | CH₃ |
| 6-OCH₃ | CH₃ |
| 6-CF₃ | CH₃ |
| 7-Cl | CH₃ |
| 7-F | CH₃ |
| 7-Br | CH₃ |
| 7-CH₃ | CH₃ |
| 7-OCH₃ | CH₃ |
| 7-CF₃ | CH₃ |
| 6-Cl | CH₂CH₃ |
| 6-F | CH₂CH₂CH₃ |
| 7-F | CH(CH₂)₂CH₃ |
| 5-F | CH(CH₃)₂ |
| 5-F | CH(CH₃)₂ |
| 6-CH₃ | CH₂CH₃ |
| 5-F | CH₂(CH₃)CH₂CH₃ |

Formulations

Useful formulations of the compounds of Formula I may be prepared in conventional ways. These include powders, tablets, syrups, etc. Suitable carriers include water, glycerol, alcohols, sorbitol, salts, citric acid, sucrose, etc. Alternatively, the compounds of Formula I may be used directly without the need for formulation.

The compound of Formula I may also be used in combination with other sweeteners such as sucrose, saccharin, L-aspartyl-L-phenyl-alanine esters and cyclamates,

Utility

The compounds of Formula I are useful as sweetening agents in a variety of foods and beverages.

For example, fruits, vegetables, juices, soft drinks, cakes, pies, ice creams, baking goods, candies, powdered drinks, beverages, gums, jellies, syrups, meats and other food and drink products may include the instant sweetener.

Alternatively, compounds of Formula I may be added directly to foods or beverages as food additives.

The quantity of compound of Formula I to be added will be dependent on the amount of the desired effect and the ingredient it is to be added to.

The sweetening property of the subject compounds are described in Table III.

TABLE III

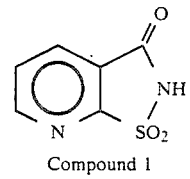

Compound 1

| Compound | Taste | After-taste Bitterness |
|---|---|---|
| 1 | sweet | no |
| saccharin | sweet | yes |

What is claimed is:

1. A method for sweetening foods and beverages, comprising the addition of a compound of Formula I:

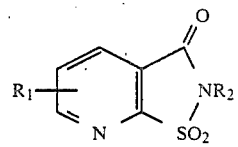

and suitable salts thereof to foods or beverages, wherein R₁ is H, Cl, F, Br, CH₃, OCH₃, or CF₃; and R₂ is H, C₁-C₄ alkyl.

2. The method of claim 1 wherein R₂ is H.

3. The method of claim 2 wherein R₁ is H.

* * * * *